US006332097B1

(12) United States Patent
Beder

(10) Patent No.: US 6,332,097 B1
(45) Date of Patent: *Dec. 18, 2001

(54) HAIR REGROWTH METHOD AND APPARATUS

(75) Inventor: Douglas S. Beder, Vancouver (CA)

(73) Assignee: 314613 B.C. Ltd., Vancouver ( * ) Notice: Subject to any disclaimer, the term of this patent is extended or adjusted under 35 U.S.C. 154(b) by 0 days.

This patent is subject to a terminal disclaimer.

(21) Appl. No.: 09/498,919

(22) Filed: Feb. 4, 2000

(51) Int. Cl.[7] ........................................ A61N 1/00
(52) U.S. Cl. ........................ 607/139; 607/115; 607/149
(58) Field of Search ....................... 607/46, 48, 50, 607/72, 75, 115, 148–154, 139; 600/372, 382, 386

(56) References Cited

U.S. PATENT DOCUMENTS 5,336,247 * 8/1994 Groux et al. ................. 607/72 X
5,344,440 * 9/1994 Stephen ........................... 607/139
6,041,262 * 3/2000 Beder ............................. 607/139

* cited by examiner

Primary Examiner—Robert L. Nasser
Assistant Examiner—Ryan Carter
(74) Attorney, Agent, or Firm—Kolisch Hartwell Dickinson McCormack & Heuser

(57) ABSTRACT

A plurality of electrodes are mounted within a hood positionable over a subject's hed to form an array of concentric electrically conductive electrode rings. The rings can be applied to an outer surface of an electrically insulating liner insertable within the hood. The array preferably comprises five rings mounted within the hood to subtend a 90° arc on both sides of a central perpendicular axis of the hood. The four upper electrodes each subtend an arc of about 15° and the fifth (lower) electrode subtends an arc of about 6°, with 6° arc gaps between each pair of electrodes on either side of the central perpendicular axis. A voltage pulse signal generator's output signal is connected across the two upper electrode pairs, with alternate electrodes being connected to one of the two output terminals of the voltage pulse generator. A voltage divider applies a reduced voltage signal to the lower electrode.

4 Claims, 4 Drawing Sheets

HAIR REGROWTH METHOD AND APPARATUS

FIELD OF THE INVENTION

This application pertains to an electrode array for use in a hair regrowth apparatus.

BACKGROUND OF THE INVENTION

Many individuals are troubled by premature baldness, receding hairlines, or other conditions in which hair is lost from the head. Over the years, a variety of chemicals have been marketed as hair regrowth aids but with mixed, generally disappointing results. Many individuals have invested considerable sums in artificial hair pieces. Some individuals have even undergone surgical hair implantation procedures requiring the exercise of highly skilled medical expertise which is generally unavailable to a wide cross-section of potential beneficiaries. It will thus be appreciated that there is a need for a reasonably inexpensive hair regrowth process capable of being administered by relatively unskilled personnel and capable of promoting hair regrowth in the widest possible population cross-section.

The prior art discloses that a variety of electrical stimuli have been employed in an effort to promote hair growth. For example, U.S. Pat. No. 861,349 issued Jul. 30, 1907 for an invention of R. E. Beaubien entitled "Apparatus for Treating the Scalp" discloses an "apparatus for promoting the growth of hair upon the human head". The apparatus appears to rely upon a combination of pneumatic, vacuum and electrical effects, in combination with the application of medicated lotions and massage to the scalp. According to Beaubien, any desirable form of electrical battery or current may be used. The present applicant however believes that this is not the case and that in order to satisfactorily promote hair regrowth, specific electrical signals must be employed.

U.S. Pat. No. 735,581 issued Aug. 4, 1903 for an invention of Pollacsek, et al. entitled "Therapeautical Apparatus" discloses a device "by means of which vibrations of diseased parts of the body can be produced". Pollacsek, et al. indicate that the device may be shaped as a cap to be placed on the head and that the cap may be introduced into a magnetic field produced by an electric current passing through the windings of an iron core. However, there is no indication of the specific nature of the electric or magnetic signals or fields employed, nor is there any suggestion that Pollacsek, et al. considered applying their device to promote hair regrowth.

U.S. Pat. No. 740,385 issued Oct. 6, 1903 for an invention of W. B. Bassell entitled "Electrotherapeutic Appliance" provides another device "adapted to subject the wearer to the action of a current of electricity for curative purposes". Bassell explains that his invention is to be utilized for the relief and cure of nervousness, insomnia, headache, and other kindred troubles. He suggests that this may be accomplished by subjecting the head of the wearer to the action of a comparatively mild current of electricity provided by a small battery. Again however there is no suggestion that Bassell considered the use of his device to promote hair regrowth, nor are any specific electrical signals discussed.

U.S. Pat. No. 3,872,859 issued Mar. 25, 1975 for an invention of Pitzen, et al. entitled "Method and Device for Stimulating the Organs Associated with the Human Scalp" examines the problem of promoting hair growth in some detail. Pitzen, et al. provide a method and apparatus in which a plurality of wave form generators output signals having frequencies varying from 230 hertz through 2650 hertz. The waveform generators are also pulsed at repetition rates varying from 3 times per second to 26 times per second. The signals so produced are applied to hand-held massaging electrodes which are in turn applied to the subject's scalp.

Published French Patent Application No. 2,484,262 of Paul Maurice Viallis provides another electrical apparatus and method for treating the human scalp to combat seborrhea, hair loss, dandruff, etc. A conductive electrode cap is fitted over the scalp and a secondary electrode is placed in contact with another area of the body. A current of the order of 8–15 mA is applied for a period of 5 to 30 minutes depending upon the type of complaint and type of treatment prescribed. The object of Viallis' invention is apparently to ionize the scalp area so that ointments or other applied treatment compositions may penetrate the scalp with greater effectiveness.

Published West German Patent Application No. 3,618,933 discloses an invention of Masaki, et al. pertaining to an electrotherapeutic device for promoting eyebrow hair growth. The apparatus is shaped to fit on a patient's head. Electrodes are applied to the eyebrows. A pulse-like current preferably having a square or trapezoid waveform is applied to the electrodes, with a biphasic action, potential-like oscillation having a frequency in the 1/500 to 1/200 second range and pulsed at a frequency of 0.5 to 2 seconds is preferably applied to the electrodes.

Two published British Patent Application Nos. 2,160,426A and 2,160,427A of Masaki appear to correspond to the West German application aforesaid, although the British applications do not appear to restrict themselves to eyebrow hair growth.

U.S. Pat. No. 3,946,745 Hsiang-Lai et al. teaches a system in which electrical pulses are applied directly to a living body, for example by attaching electrodes to the body by means of an acupuncture needle or spring-loaded earring.

German Patent Application DE 29 52 850 A1 teaches the use of electromagnetic pulsating fields for stimulating the body functions furthering the growth of hair. Frequencies in the 400–420 hertz range are mentioned, with the subject undergoing continuous exposure to the fields, for example by having the subject carry a battery powered apparatus on his/her person.

French Patent No. 1,350,890 teaches a hair dryer having an electrode structure to which a high frequency voltage generator is electrically coupled in order to apply an intense high frequency electric field to the hair so as to heat and evaporate water from the hair. The patent mentions that the applied field also has a stimulating effect on the cells of the skin and improves blood circulation, which is favourable to the metabolism and to healthy growth of hair.

Although not wishing to be bound by any theory, the inventors believe that dormant body hair cells (i.e. hair cells from which hair is not actively growing) may be electrically stimulated to promote active hair growth from such cells. More particularly, the inventors believe that hair regrowth can be promoted if the body's hair cells are stimulated by subjecting them to a low voltage pulse train having a pulse repetition frequency in the range of about 5 to 35 hertz. The higher portion of this frequency range is considered appropriate for subjects who exhibit normal or hyperactive energy levels. The lower portion of the frequency range is considered appropriate for individuals who exhibit hypoactive or slow metabolism energy levels.

SUMMARY OF THE INVENTION

In accordance with the preferred embodiment, the invention provides a plurality of electrodes mounted within a hood positionable over the subject's head to form an array of concentric electrically conductive electrode rings. The rings can be applied to an outer surface of an electrically insulating liner insertable within the hood. The array preferably comprises five rings mounted within the hood to subtend a 90° arc on both sides of a central perpendicular axis of the hood. The four upper electrodes each subtend an arc of about 15° and the fifth (lower) electrode subtends an arc of about 6°, with 6° arc gaps between each pair of electrodes on either side of the central perpendicular axis. A voltage pulse generator's output signal is applied across the two upper electrode pairs, with alternate electrodes being connected to one of the two output terminals of the voltage pulse generator. A voltage divider applies a reduced voltage signal to the lower electrode.

DETAILED DESCRIPTION OF THE PREFERRED EMBODIMENT

Figure 1A:
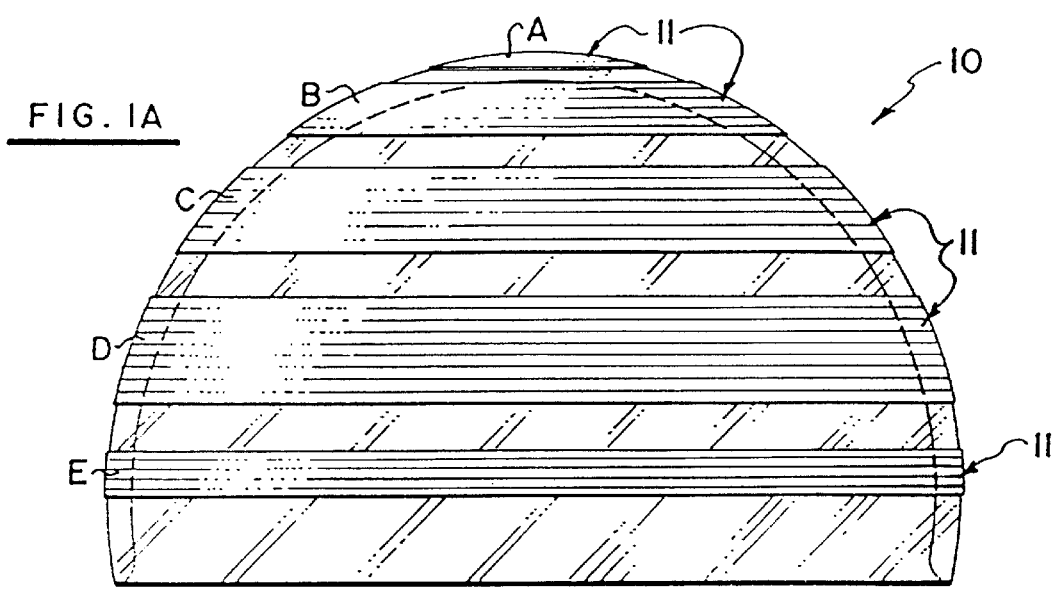
FIG. 1A is an elevation view of a schematically represented hood liner bearing an electrode array configured for use in practicing the invention.
Figure 1B:
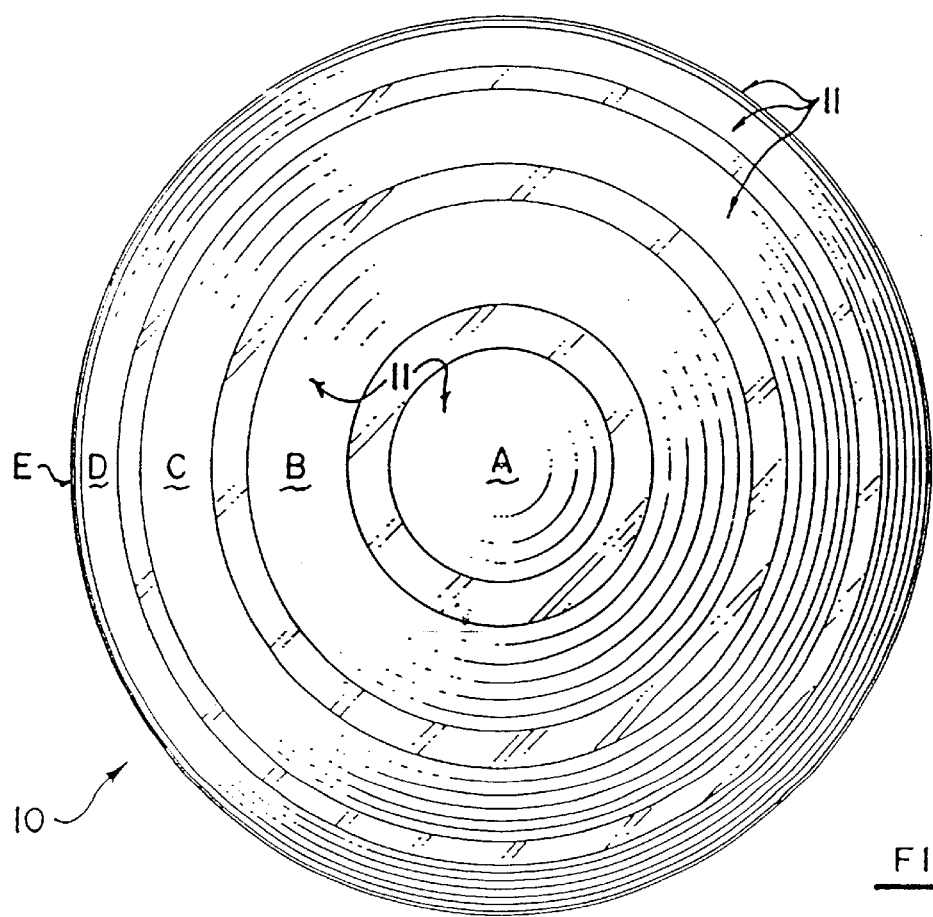
FIG. 1B is a top view of the FIG. 1A structure.
Figure 2:
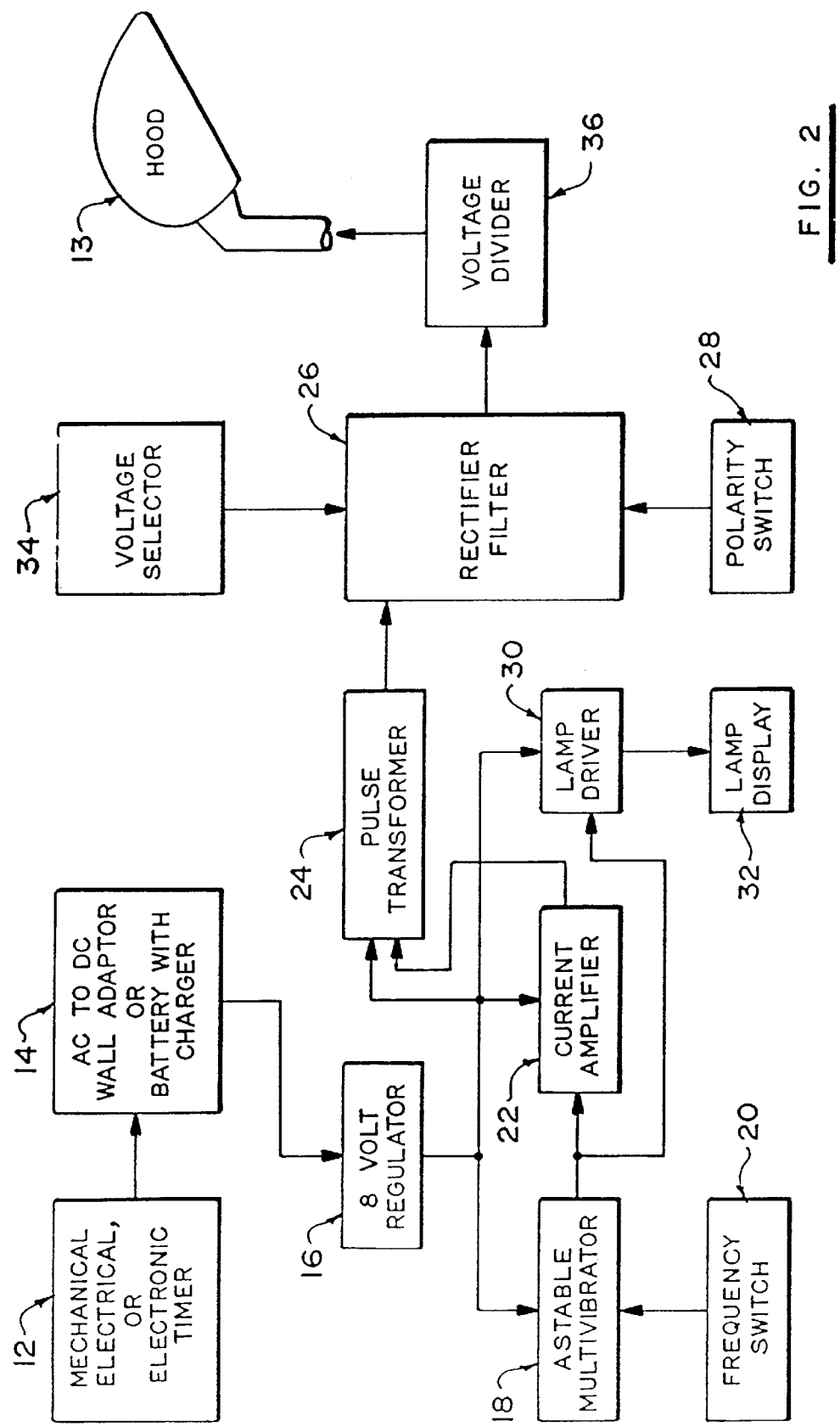
FIG. 2 is a block diagram of a hair regrowth apparatus constructed in accordance with the preferred embodiment of the invention.

As shown in FIGS. 1A, 1B and 2, the exterior surface of hood liner 10 carries a plurality of electrodes 11. When liner 10 is inserted within hood 13 and the hood placed over a subject's head, electrodes 11 are positioned closely proximate to, but do not touch the subject's scalp.

The apparatus is turned on and off with the aid of a mechanical, electrical or electronic timer 12 (FIG. 2) operatively connected to power supply 14 which may be a conventional 110 volt A.C. to 12 volt D.C.transformer. The 12 volt D.C. signal output by power supply 14 is regulated down to 8 volts D.C. by voltage regulator 16 and the resultant 8 volt D.C. signal is then used to power the remaining electronic components depicted in FIG. 2. Instead of directly coupling a 110 volt A.C. power source to the circuitry as aforesaid, one may alternatively use power supply 14 to charge a 12 volt D.C. battery. The charged battery can then be used to fulfill the apparatus' power requirements and power supply 14 can be disconnected from the 110 volt A.C. power source while the apparatus is in use with a subject.

A voltage pulse generator means 18, such as an astable multivibrator, is electrically coupled to electrodes 11. Pulse generator 18 applies a low voltage train of short duration pulses to electrodes 11 at a selectable pulse repetition frequency. Specifically, frequency selector switch 20 is electrically coupled to pulse generator 18 to enable the operator to vary the pulse repetition frequency within the preferred range of about 5 to 35 hertz. Lamp driver 30 provides a visual indication, via lamp 32, of the selected pulse repetition frequency (i.e. lamp 32 blinks on and off at the selected frequency).

The low voltage pulse train output by pulse generator 18 is amplified by current amplifier 22 and then presented to pulse transformer 24 which outputs one of two operating voltages (55 volts peak-to-peak; or, 110 volts peak-to-peak). A "signal polarity selector means"; namely, rectifier/filter 26, is electrically coupled between pulse transformer 24 and electrodes 11, thereby enabling the operator to vary the polarity of the signals output by pulse transformer 24 through manual selection of one of two positions for polarity switch 28. A "voltage selector means"; namely, two position switch 34 is provided to enable the operator to select one of the two operating voltages aforesaid for the pulse train applied to electrodes 11.

Figure 3:
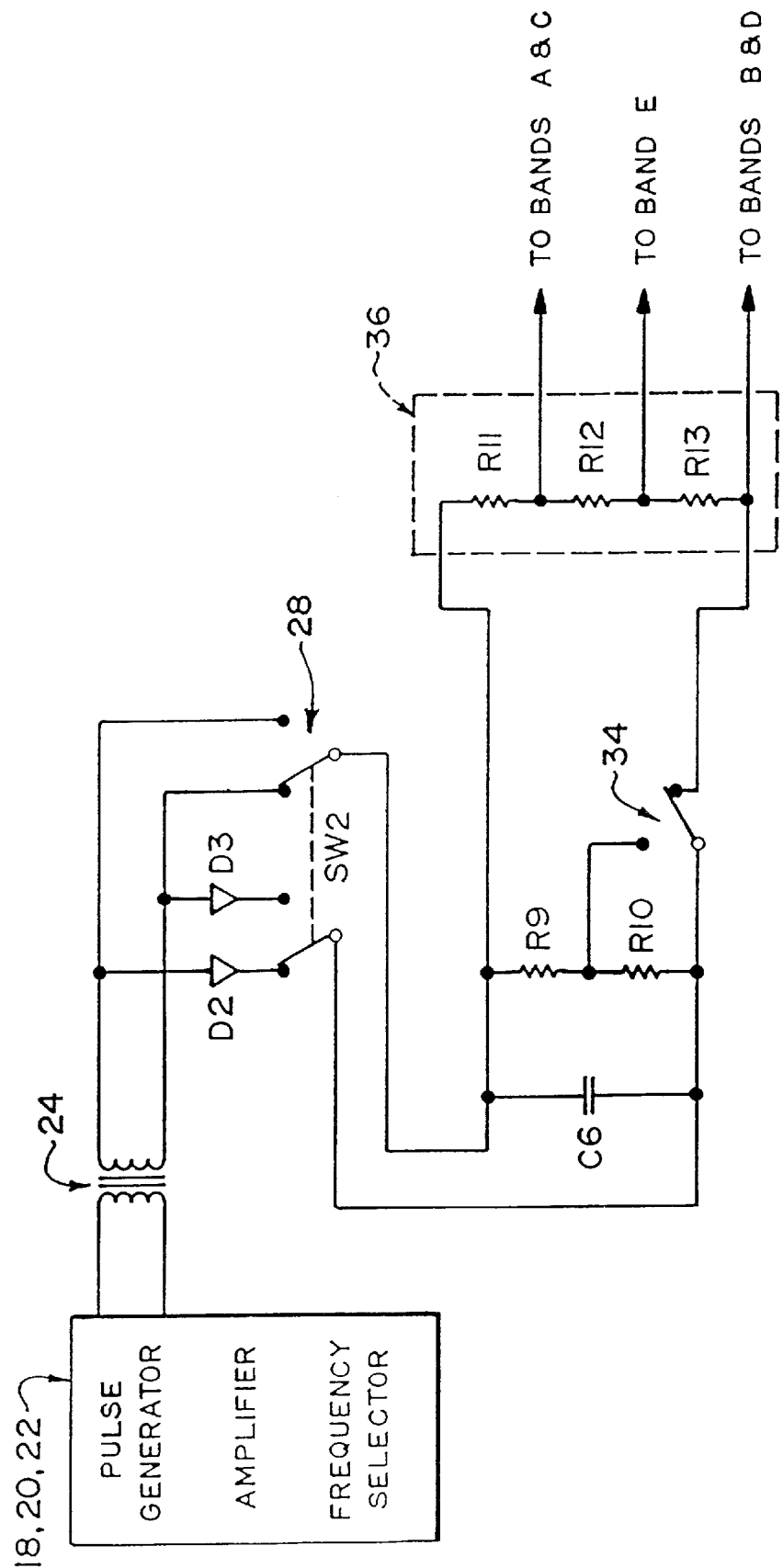
FIG. 3 is a partial schematic/block diagram depicting further details of the circuitry utilized with the preferred electrode array.
Figure 4:
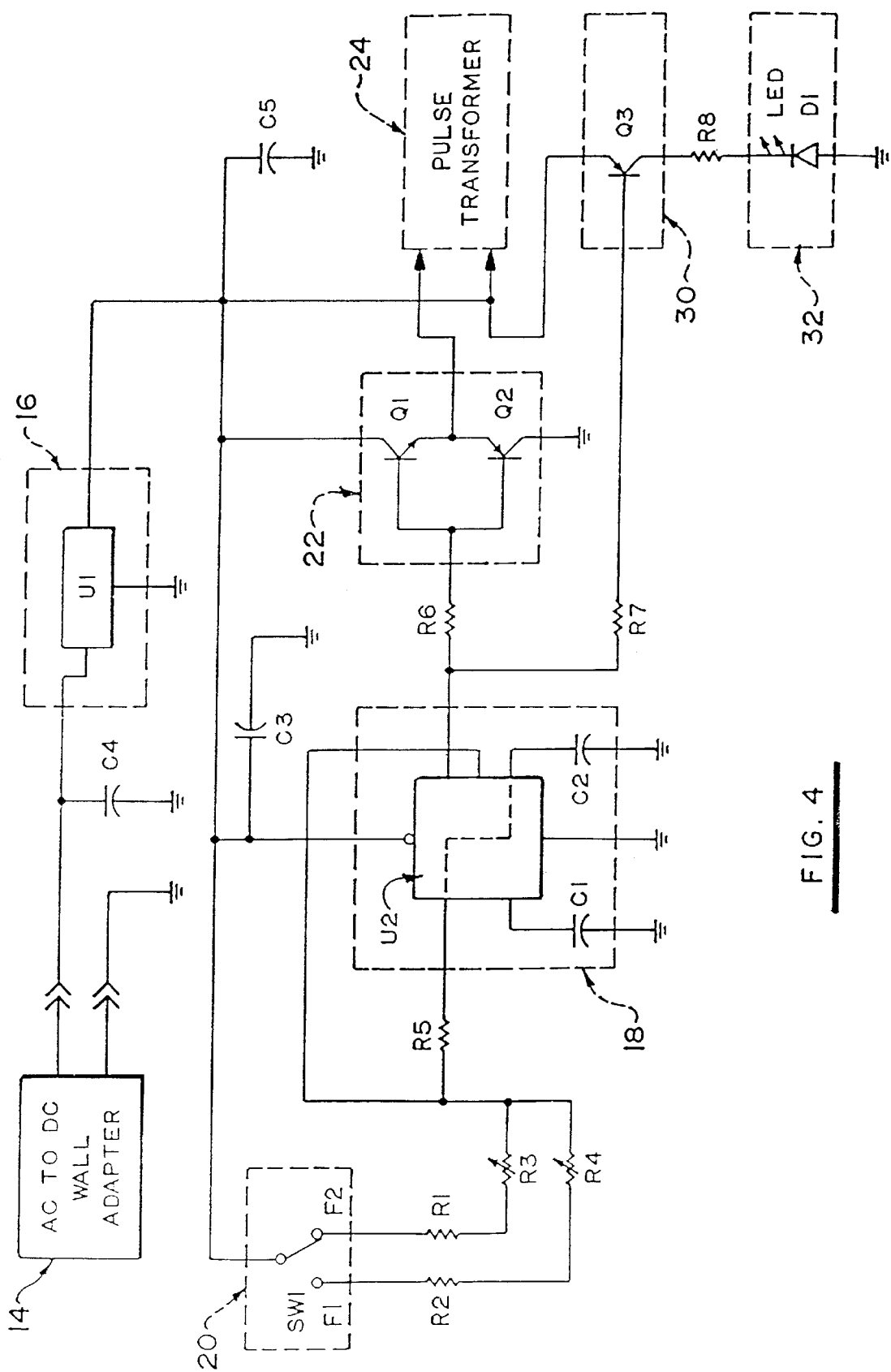
FIG. 4 is an electronic circuit schematic diagram depicting additional details of the preferred apparatus.

Further details of the preferred circuitry are now provided with reference to FIGS. 3 and 4. The 12 volt D.C. signal output by power supply 14 is electrically coupled to voltage regulator 16 which, in the preferred embodiment, is an LM7808 integrated circuit 8 volt regulator with internal current limiting, thermal shutdown capability and safe area compensation for the internal pass transistor. Capacitors C4 and C5 respectively provide low frequency filtering for the input and output of regulator 16, which produces an 8 volt D.C. output signal used to power the remaining electronic components.

Astable multivibrator 18 is a NE555 integrated circuit pulse generator. The trigger input of astable mulfivibrator 18 is connected to the threshold input thereof (represented by the dashed line show in integrated circuit U2 in FIG. 4) in order to continuously retrigger the circuit for astable operation thereof. Resistors R1, R2 and R5, together with potentiometer R3 and R4 and timing capacitors C1 and C2 control the frequency of the pulse train output by astable multivibrator 18. The output frequency is selected by manual positioning of switch SW1 (reference No. 20 in FIG. 1) which is a single pole, double throw switch (assuming configuration of the apparatus to supply pulse trains of two different frequencies; comparable switching arrangements can be provided if the apparatus is to be configured for use with three or more such frequencies). When switch SW1 is in the "F1" position, astable multivibrator 18 produces a low voltage, pulse train at a first frequency. When switch SW1 is in the "F2" position astable multivibrator 18 produces a low voltage, pulse train at a second frequency. More particularly, when switch SW1 is in the "F1" position, the steady state frequency of the voltage pulse train output by astable multivibrator 18 is determined by:

$$F1 = \frac{1}{T1} = .693(R2 + R4 + R5)C2$$

Similarly, when frequency selector switch SW1 is in the "F2" position, the steady state frequency of the voltage pulse train output by astable multivibrator 18 is determined by:

$$F2 = \frac{1}{T2} = .693(R1 + R3 + R5)C2$$

The frequency selected is visually indicated by flashing light emitting diode D1, which is driven through current limiting resistor R7 and inverting amplifier transistor Q3. Resistor R8 provides current limiting for light emitting diode D1.

Capacitor C1 is used to bypass pin 5 of the astable multivibrator 18 to ground, preventing noise from altering the width of the pulses output by astable multivibrator 18. Capacitor C3 is a bypass capacitor which eliminates high frequency noise on the power line.

The low voltage pulse train output by astable multivibrator 18 passes to a current amplifier 22 comprising transistors Q1 and Q2, which are configured to operate in a class B switching mode to provide the higher peak currents passed through pulse transformer 24. More particularly, when pulse transformer 24 is switched on, a pulse is imposed on the transformer primary winding. Because the transformer provides D.C. isolation, the higher voltage end of the transformer can safely be used to produce a positive or negative-going pulse through the polarity selector means comprising pulse transformer 24 together with a first rectifier means (i.e. diode D2 shown in FIG. 3), a second rectifier means (i.e. diode D3 shown in FIG. 3) and polarity switch SW2 (reference No. 28 in FIG. 1). When switch SW2 is in the "positive" polarity position, diode D2 in combination with filter capacitor C6 and discharge resistor R9 shape the pulses output by switching transformer 24, while blocking negative-going portions of the pulse train. Similarly, when polarity selector switch SW2 is in the "negative" polarity position, diode D3 blocks positive-going portions of the pulse train. The voltage output across resistor R9 is coupled to the electrodes within hood 13. Limit resistor R10 and voltage selector switch SW3 (reference No. 34 in FIG. 1) enable the operator to select between one of two operating voltages (55 volts peak-to-peak; or, 110 volts peak-to-peak) in the preferred embodiment.

Reverting to FIGS. 1A and 1B, the preferred electrode array consists of five electrodes 11, each comprising a thin band of conductive material such as copper foil. The bands are applied to form approximately concentric rings on the outer surface of hood-shaped liner 10, which is formed of an electrically insulating material such as plastic. Liner 10 supports the electrode bands and prevents them from contacting the subject when liner 10 is inserted within hood 13. More particularly, hood 13 (which may be a conventional commercial hair dryer hood) is placed over the subject's head so that the inner (i.e. non-electrode bearing) surface of liner 10 is adjacent the subject's head. Typically, the subject's scalp is separated from the inner surface of liner 10 by a gap of several centimeters.

The number of bands, the width of each band, the spacing between each band, and the relative placement of each band on liner 10 are selected so that the electric fields imposed on the subject's scalp under each band are approximately equal and to prevent imposition of excessive electric fields on the subject's scalp outside the region thereof adjacent electrodes 11. In the preferred embodiment, electrodes 11 subtend a 180° arc (i.e. 90° on either side of the central perpendicular axis of hood 13 as seen in FIG. 1A), with the four upper electrodes each subtending arcs of about 15° and the fifth (lowermost) electrode subtending an arc of about 6°, with 6° arc gaps between each pair of electrodes on either side of the central perpendicular axis.

The full voltage signal output by rectifier/filter 26 is applied across electrode pair A and B; and, across electrode pair C and D. A voltage divider 36 supplies a half-strength voltage signal for application to electrode E. This reduced voltage assists in preventing imposition of excessive electric fields to the subject's scalp outside the region thereof adjacent to the electrodes, as mentioned above. As shown in FIG. 3, voltage divider 36 comprises three series-connected resistors $R_{11}$, $R_{12}$, and $R_{13}$. Electrode bands A and C are electrically connected to the voltage dividing point between $R_{11}$ and $R_{12}$, band E is electrically connected to the voltage dividing point between $R_{12}$ and $R_{13}$, and bands B and D are electrically connected to the opposite end of $R_{13}$. In the preferred embodiment, the resistance values of $R_{11}$ and $R_{13}$=1.2 MΩ and $R_{12}$ =0.39 MΩ.

FIG. 3 also shows further details of rectifier/filter 26 polariy switch 28 and voltage selector switch 34. Specifically, rectifier/filter 26 preferably includes a capacitor $C_6$ connected in parallel across a pair of series-connected resistors $R_9$, $R_{10}$; with the capacitance value of $C_6$=1.8 pf, and the resistance values of $R_9$ and $R_{10}$=0.56 MΩ. Polarity switch 28 preferably includes a pair of diodes $D_2$, $D_3$ which may be alternatively switched into the circuit path emanating from either one of the two output leads of pulse transformer 24. (The polarity of the voltage signal applied across any pair of electrode bands is the sign of the voltage difference across those electrodes. In the case of the FIG. 1 electrode array, the polarity is the sign of the voltage applied to electrode band A.) Voltage selector switch 34 is coupled across $R_{10}$ such that, in one position of switch 34 the voltage developed across $R_9$ is applied to voltage divider 36, and in the other position of switch 34 the voltage developed across the series-connected combination of $R_9$ and $R_{10}$ is applied to voltage divider 36.

In operation, the subject's head is positioned within hood 13, so that electrodes 11 lie closely proximate to, but do not touch the subject's scalp. Power is applied to the circuit and switches 20, 28 manually positioned to select a desired signal output frequency and polarity. Signals of the selected frequency and polarity are applied to electrodes 11 for about 12 minutes, following which the power is disconnected and hood 13 removed from the subject's head. Repetitive treatments over many weeks will be required, depending upon the individual characteristics of the particular subject.

An entire hair regrowth/hair loss mitigation treatment cycle will typically span about 32 weeks, during which time the subject undergoes one or two 12 minute treatments as aforesaid per week. The following table provides the weekly treatment frequency, the signal output polarity and the voltage level preferably employed (according to empirical determinations) during each week of the 32 week treatment cycle:

|  | Number of Treatments | Polarity | Voltage Level |
| --- | --- | --- | --- |
| 1st week | 2 | Positive | 110 v. |
| 2nd week | 2 | Positive | 110 v. |
| 3rd week | 1 | Negative | 110 v. |
| 4th week | 1 | Negative | 110 v. |
| 5th week | 1 | Negative | 110 v. |
| 6th week | 1 | Negative | 110 v. |
| 7th week | 1 | Negative | 110 v. |
| 8th week | 1 | Negative | 110 v. |
| 9th week | 1 | Negative | 110 v. |
| 10th week | 1 | Negative | 110 v. |
| 11th week | 1 | Negative | 110 v. |
| 12th week | 1 | Negative | 110 v. |
| 13th week | 1 | Negative | 110 v. |
| 14th week | 1 | Negative | 110 v. |
| 15th week | 1 | Negative | 110 v. |
| 16th week | 1 | Negative | 110 v. |
| 17th week | 2 | Positive | 55 v. |
| 18th week | 2 | Positive | 110 v. |
| 19th week | 1 | Negative | 55 v. |
| 20th week | 1 | Negative | 110 v. |
| 21st week | 1 | Negative | 55 v. |
| 22nd week | 1 | Negative | 110 v. |
| 23rd week | 1 | Negative | 55 v. |
| 24th week | 1 | Negative | 110 v. |
| 25th week | 1 | Negative | 55 v. |
| 26th week | 1 | Negative | 110 v. |
| 27th week | 1 | Negative | 55 v. |
| 28th week | 1 | Negative | 110 v. |
| 29th week | 1 | Negative | 55 v. |

-continued

|  | Number of Treatments | Polarity | Voltage Level |
|---|---|---|---|
| 30th week | 1 | Negative | 110 v. |
| 31st week | 1 | Negative | 55 v. |
| 32nd week | 1 | Negative | 110 v. |

Some subjects may respond more favorably to alternative signal polarities than those set forth above. Accordingly, based upon professional review, the treatment regimen may be varied by, for example, replacing two of the negative polarity treatments with two positive polarity treatments and then returning to negative polarity treatments as prescribed for the balance of the treatment cycle.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

I claim:

1. An electrode array for a hair regrowth apparatus, said apparatus comprising voltage pulse generator means for electrical coupling to said electrode array for application thereto of a low voltage pulse train and frequency selector means for electrical coupling to said voltage pulse generator means for varying the pulse repetition frequency of said pulse train, said electrode array comprising a plurality of concentric electrically conductive rings mounted within a hood positionable over a subject's head.

2. An electrode array as defined in claim 1, wherein said array comprises five rings mounted within said hood to subtend a 90° arc on both sides of a central perpendicular axis of said hood.

3. An electrode array as defined in claim 2, wherein said array further comprises first, second, third and fourth upper electrodes each subtending an arc of about 15° and a fifth lower electrode subtending an arc of about 6°, with 6° arc gaps between each pair of said electrodes, on either side of said central perpendicular axis.

4. An electrode array as defined in claim 3, wherein said voltage pulse generator means output signal is applied across said first and third electrodes and across said second and fourth electrodes and further comprising voltage divider means for applying a reduced voltage signal to said fifth electrode.

* * * * *